US00PP10917P

United States Patent [19]

Bergman

[11] Patent Number: Plant 10,917

[45] Date of Patent: May 25, 1999

[54] HIBISCUS PLANT NAMED 'CARISMA ORANGE'

[75] Inventor: Wendy R. Bergman, Lehigh Acres, Fla.

[73] Assignee: Yoder Brothers, Inc., Barberton, Ohio

[21] Appl. No.: 08/995,362

[22] Filed: Dec. 29, 1997

[51] Int. Cl.[6] ..... A01H 5/00

[52] U.S. Cl. ..... Plt./67.8

[58] Field of Search ..... Plt./67.8

[56] References Cited

PUBLICATIONS

Usher. The Wordsworth Dictionary of Botany. Wordsworth Editions Ltd., Ware, p. 274, 1966.

*Primary Examiner*—Elizabeth Kemmerer

*Attorney, Agent, or Firm*—C. A. Whealy

[57] ABSTRACT

A new and distinct cultivar of Hibiscus plant named 'Carisma Orange', characterized by its dark green leaves; upright and outwardly spreading, uniform and symmetrical plant habit that is appropriate for container production; floriferousness with numerous intense orange-colored flowers with red throats; good resistance to flower bud abscission; and excellent postproduction longevity.

1 Drawing Sheet

The present invention relates to a new and distinct cultivar of Hibiscus, botanically known as *Hibiscus rosa-sinensis*, and hereinafter referred to by the cultivar name Carisma Orange. It is proposed that the new Hibiscus will be marketed under the name Paradise Breeze.

The new cultivar is a product of a planned breeding program conducted by the inventor in Alva, Fla. The objective of the breeding program is to create new Hibiscus cultivars having uniform and compact plant habits appropriate for container production, early and uniform flowering, numerous flowers per lateral branch, desirable flower color, resistance to flower bud abscission, and good postproduction longevity.

The new cultivar originated from a cross made by the inventor in Alva, Fla., of a proprietary *Hibiscus rosa-sinensis* selection, designated as code number 602, as the female, or seed, parent with a proprietary Hibiscus selection, designated as code number 211, as the male, or pollen, parent. The cultivar Carisma Orange was discovered and selected by the inventor as a flowering plant within the progeny of the stated cross in a controlled environment in Alva, Fla., on May 9, 1994.

Compared to plants of the female parent, the proprietary Hibiscus selection code number 602, plants of the new Hibiscus are more compact, flower about two weeks earlier, are more floriferous, and have a darker orange flower color. Plants of the new Hibiscus differ in flower color and have a less ruffled flower margin compared to plants of the male parent, the proprietary Hibiscus selection code number 211.

Asexual reproduction of the new cultivar by terminal cuttings taken in a controlled environment in Alva, Fla., has shown that the unique features of this new Hibiscus are stable and reproduced true to type in successive generations.

The cultivar Carisma Orange has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Carisma Orange'. These characteristics in combination distinguish 'Carisma Orange' as a new and distinct cultivar:

1. Dark green leaves.
2. Upright and outwardly spreading, uniform and symmetrical plant habit that is appropriate for container production.

3. Very freely flowering, numerous intense orange-colored flowers with red throats.
4. Good resistance to flower bud abscission.
5. Excellent postproduction longevity.

Plants of the new Hibiscus can be compared to plants of the nonpatented cultivar Euterpe. However, in side-by-side comparisons conducted in Alva, Fla., plants of the new cultivar differ from plants of the cultivar Euterpe in the following characteristics:

1. Plants of the new Hibiscus are more compact than plants of the cultivar Euterpe.
2. Plants of the new Hibiscus have smaller but more numerous flowers than plants of the cultivar Euterpe.
3. Plants of the new Hibiscus have a more intense orange flower color than plants of the cultivar Euterpe.
4. Flower throat color of plants of the new Hibiscus is lighter red in color than plants of the cultivar Euterpe.
5. Plants of the new Hibiscus flower about 18 days earlier than plants of the cultivar Euterpe.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of typical plant of 'Carisma Orange'.

The photograph at the bottom of the sheet comprises a close-up view of a typical flower of 'Carisma Orange'. Flower and foliage colors in the photographs may appear different from the actual colors due to light reflectance.

DETAILED BOTANICAL DESCRIPTION

The following observations, measurements and values describe plants grown in Alva, Fla., and Keller, Tex., in 28-cm containers during the summer and early autumn with day temperatures ranging from 16 to 35° C. and night temperatures ranging from 10 to 24° C. In the description, color references are made to The Royal Horticultural Society Colour Chart except where general terms of ordinary dictionary significance are used.

Botanical Classification: *Hibiscus rosa-sinensis* cultivar Carisma Orange.

Parentage:

*Female or seed parent.*—*Hibiscus rosa-sinensis* proprietary selection designated as code number 602.

*Male or pollen parent.*—*Hibiscus rosa-sinensis* proprietary selection designated as code number 211.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright and outwardly spreading, inverted triangle, uniform and symmetrical plant habit. Moderate vigor.

*Branching habit.*—Freely branching, usually six to seven lateral branches develop after removal of terminal apex.

*Plant height, soil level to top of flowers.*—About 45 cm.

*Plant diameter, area of spread.*—About 53 cm.

*Lateral branch description.*—Length: About 38 cm. Diameter: About 1.1 cm. Texture: Immature, smooth; woody with age.

*Color.*—Immature: Green, 144A. Mature: Gray.

Foliage description:

*Arrangement.*—Alternate, single.

*Length.*—About 9 cm.

*Width.*—About 8.5 cm.

*Shape.*—Ovate to cordate.

*Apex.*—Acute.

*Base.*—Cordate.

*Margin.*—Crenate, older leaves deeply lobed.

*Texture.*—Glabrous and glossy on both surfaces.

*Color.*—Young foliage, upper surface: Brighter and greener than 146A. Young foliage, lower surface: 146A. Mature foliage, upper surface: Dark green, darker than 147A. Mature foliage, lower surface: Slightly darker than 147B.

*Petiole.*—Length: About 4 cm. Diameter: About 3.5 mm. Texture: Smooth or with very fine pubescence on upper surface. Color: Close to 146A.

Flower description:

*Natural flowering season.*—Usually spring and summer or during periods of warm weather.

*Flower arrangement.*—Flowers arranged singly at terminal leaf axils. Very freely flowering with usually five to six flower buds and/or open flowers per terminal apex. Flowers flat and face upright.

*Flower appearance.*—Star-shaped single, small in size. Intense orange-colored petals with red throat. Flowers are open for about one day before closing. Flowers self-cleaning.

*Flower diameter.*—About 10 cm.

*Flower bud* (*just before showing color*).—Rate of opening: About one day depending on temperatures. Length: About 1.5 cm. Diameter: About 8 mm. Shape: Columnar, oblong.

*Petals.*—Texture: Crepe, ruffled. Arrangement: Corolla consists of five petals that overlap. Shape: Spatulate with rounded apex. Margin: Entire, but slightly ruffled. Length: About 6 cm. Width: About 4.5 cm. Color: Upper surface: 33A. Lower surface: 34A. Throat: 46A.

*Sepals.*—Appearance: Six sepals fused into a star-shaped calyx. Shape: Linear. Texture: Smooth. Color, outer surface: 146A.

*Peduncles.*—Length: About 4 cm. Diameter: About 3.5 mm. Angle: Upright. Strength: Strong, rigid. Color: 146A/144A.

*Reproductive organs.*—Androecium: Stamen number: Numerous. Stamen length: About 5 mm. Anther shape: Globular. Anther size: About 1 mm. Amount of pollen: Abundant. Pollen color: 21A. Gynoecium: Pistil length: About 7 cm. Style color: Apex: 51B. Base: 46A to 47A. Stigma number: Five. Stigma shape: Round. Stigma diameter: About 3 mm. Stigma color: 46A. Ovary color: Light green darker than 154A.

Disease resistance: No known Hibiscus diseases observed to date on plants grown under commercial greenhouse conditions.

Seed production: If cross-pollinated, seed production may be observed. Usually one to twenty seeds per capsule.

It is claimed:

1. A new and distinct Hibiscus plant named 'Carisma Orange', as illustrated and described.

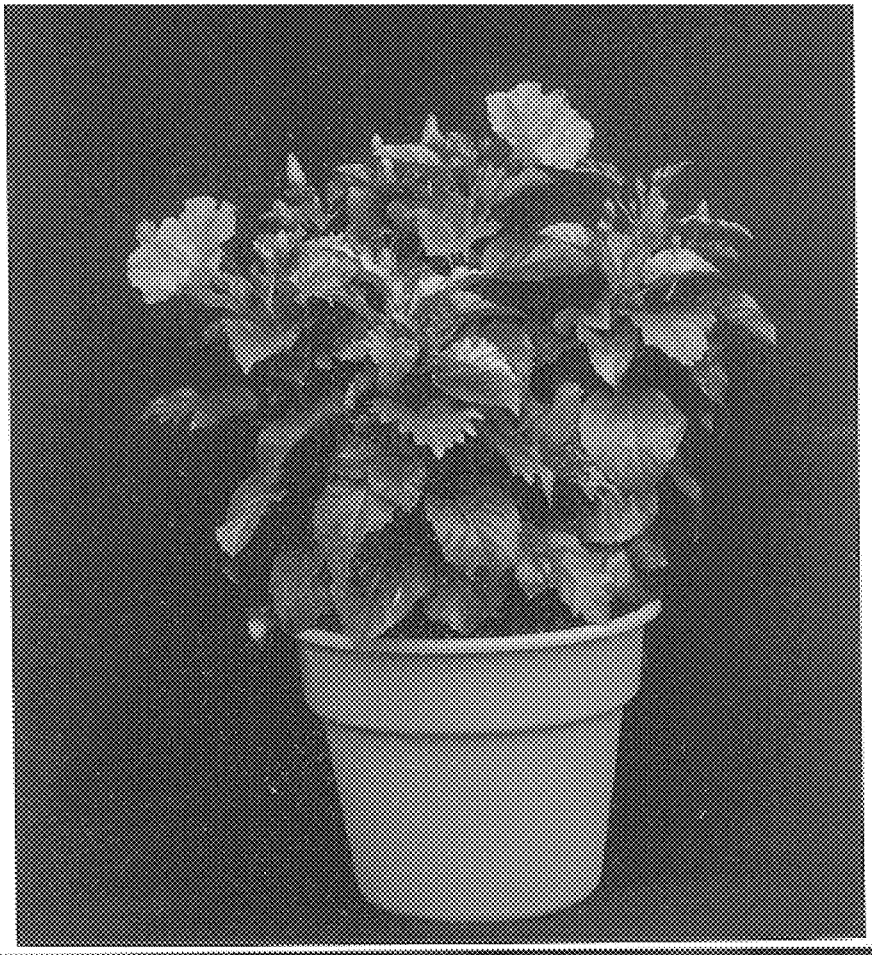
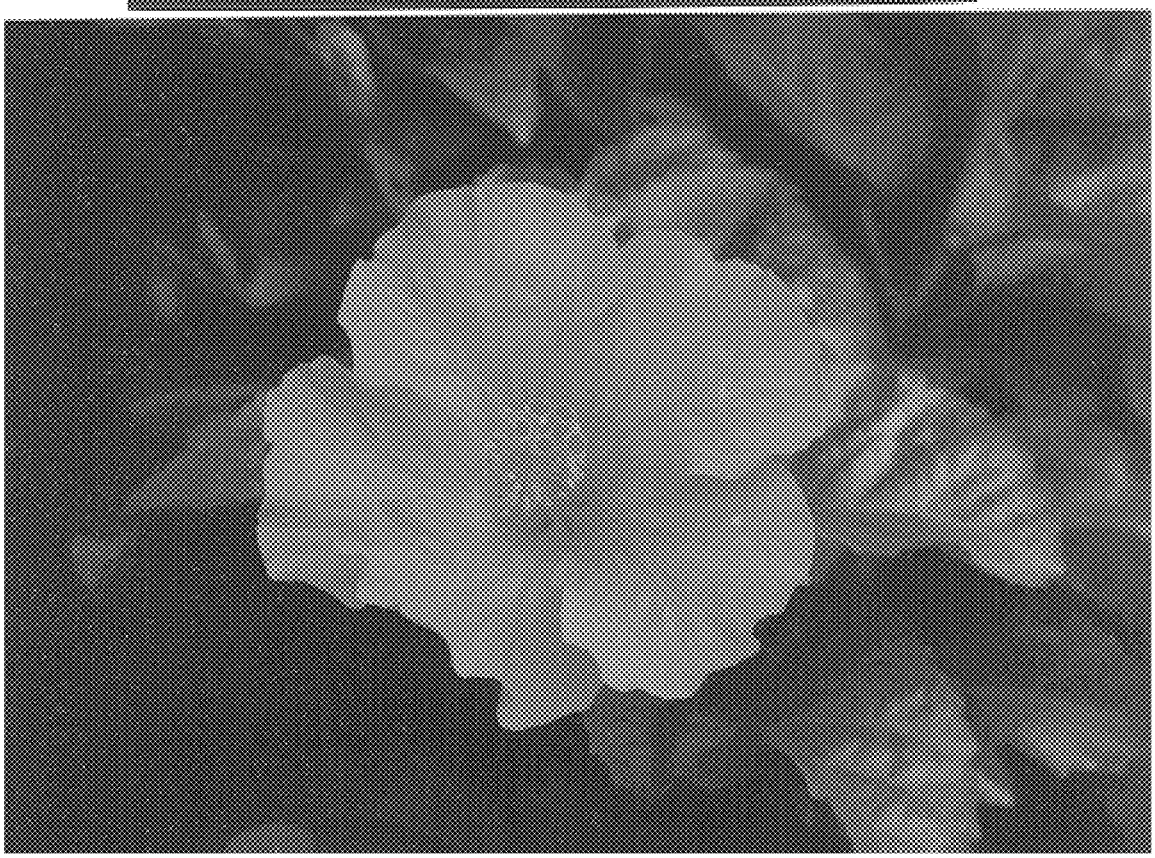

* * * * *